(12) United States Patent
Garrett et al.

(10) Patent No.: US 11,808,709 B1
(45) Date of Patent: Nov. 7, 2023

(54) METHOD FOR TESTING AND CORRECTING PHASE SEPARATION IN ETHANOL BASED FUELS

(71) Applicant: Mandatory Fuel Management, LLC, Baton Rouge, LA (US)

(72) Inventors: Gaines Garrett, Baton Rouge, LA (US); David Tiede, Baton Rouge, LA (US)

(73) Assignee: MANDATORY FUEL MANAGEMENT, LLC, Baton Rouge, LA (US)

( * ) Notice: Subject to any disclaimer, the term of this patent is extended or adjusted under 35 U.S.C. 154(b) by 730 days.

(21) Appl. No.: 16/817,947

(22) Filed: Mar. 13, 2020

Related U.S. Application Data

(60) Provisional application No. 62/818,386, filed on Mar. 14, 2019.

(51) Int. Cl.
| | | |
|---|---|---|
| *G01N 21/78* | (2023.08) | |
| *G01N 31/22* | (2023.08) | |
| *G01N 33/28* | (2023.08) | |
| *G01N 21/75* | (2006.01) | |

(52) U.S. Cl.
CPC ............ *G01N 21/78* (2013.01); *G01N 31/222* (2013.01); *G01N 33/2847* (2013.01); *G01N 2021/755* (2013.01)

(58) Field of Classification Search
CPC ... G01N 21/78; G01N 31/222; G01N 33/2847; G01N 2021/755
USPC ................ 436/39, 40, 60, 164, 165; 422/400
See application file for complete search history.

(56) References Cited

U.S. PATENT DOCUMENTS

| | | | | |
|---|---|---|---|---|
| 4,578,357 | A * | 3/1986 | Melpolder | G01N 31/221 436/39 |
| 5,585,550 | A * | 12/1996 | Frank | G01N 33/2847 141/94 |
| 6,376,250 | B1 * | 4/2002 | Mohtadi | G01N 21/80 436/39 |
| 9,557,314 | B2 * | 1/2017 | Jarvie et al. | G01N 33/2811 |
| 2015/0218473 | A1 * | 8/2015 | Vanover et al. | B60K 15/00 44/453 |

FOREIGN PATENT DOCUMENTS

| | | | |
|---|---|---|---|
| WO | 2008/064010 | A2 * | 5/2008 |
| WO | 2021/130536 | A1 * | 7/2021 |

* cited by examiner

*Primary Examiner* — Maureen Wallenhorst
(74) *Attorney, Agent, or Firm* — Ted M. Anthony; Sarah B. Dupont

(57) ABSTRACT

A process, or method, for testing ethanol-based fuel for phase separation and free-standing water, and then correcting the phase separation within the ethanol-based fuel. A method of introducing a desired amount of a chemical into suspension based on an amount of free-standing water that is within the ethanol-based fuel in order to treat and remove any and all amount of free-standing water that is remaining within the suspension.

6 Claims, 6 Drawing Sheets

METHOD FOR TESTING AND CORRECTING PHASE SEPARATION IN ETHANOL BASED FUELS

CROSS REFERENCES TO RELATED APPLICATION

Priority of U.S. Provisional Pat. Application Serial No. 62/818,386, filed Mar. 14, 2019, incorporated herein by reference, is hereby claimed.

STATEMENTS AS TO THE RIGHTS TO THE INVENTION MADE UNDER FEDERALLY SPONSORED RESEARCH AND DEVELOPMENT

None

BACKGROUND OF THE INVENTION

1. Field of the Invention

The present invention pertains to a process, or method, for testing ethanol-based fuel for phase separation and free-standing water, and then correcting said phase separation within said ethanol-based fuel. More particularly, the present invention pertains to a method of introducing a desired amount of a chemical into suspension based on an amount of free-standing water that is within the fuel in order to remove any and all amount of free-standing water within said suspension.

2. Brief Description of the Prior Art

Phase separation is an unintended consequence of government mandated introduction of ethanol into unleaded gasoline. As little as 0.5% water by volume in suspension of ethanol-based fuels will cause phase separation. During the phase process, water begins to fall out of the fuel and takes the ethanol with it. This results in fuel that does not contain enough octane to remain burnable.

There are many ways in which water can enter into an underground storage tank, where fuel is stored, and begin the phase process. For example, the age of the tanks, condensation on the side of the walls of the tanks, transport issues, and storm water intrusion can all lead to phase separation.

The issues that are typically associated with phase separation have created a significant problem for retail service stations across the country. Fuel loss and down time are the leading causes of lost revenue. For example, in 2016, there were approximately 154,535 convenience stores in the United States, and those stores generated approximately $550 billion in sales. That is a daily average sale of about $9,500.00.00 per day. However, phase separation issues can result in station downtime of about two (2) to five (5) days and sometimes even longer.

Currently, many large chains will order a fuel pump to come out when experiencing a phase event. The phased fuel is removed by a transportation company and often is sold back to the refinery as what is known as "trans-mix," which is a mixture of refined products, typically gas, diesel, water, and other contaminates. The tank is then cleaned, and a new load of fuel is dropped, or delivered, from a refinery (with the hope that the contractor removed all of the water out of the tank). This process can take about two (2) to five (5) days, and the cost can be upwards of approximately $20,000 to $30,000 per event.

Filtration, or fuel polishing, is another method currently being used today. This process can take many hours, and in a closed loop filtration system, there is no guarantee that all of the water will be removed from the tank. The downtime for this process typically ranges from about one (1) to two (2) days.

As such, there is a need for a solution that can cure this problem without any loss of fuel and can reduce store downtime from days to just a few hours. Thus, the present invention pertains to a process that saves fuel, reduces downtime, and most importantly, saves store operations money during a phase event.

SUMMARY OF THE INVENTION

The present invention pertains to a method, or process, of testing fuel for phase separation and free-standing water within a fuel tank. If the fuel is deemed to be phase separated, then all free-standing water and emulsified fuel is removed from said tank. A chemical is then introduced into suspension based on a pre-determined mixing ratio. Said tank is then agitated in order to ensure that said chemical is evenly dispersed within said tank. Then, the fuel is tested for any water in suspension. If necessary, an additional amount of said chemical is added until the fuel shows no signs of water in suspension. As a result, the process of the present invention can last about two (2) to four (4) hours from start to finish, thereby saving customers in excess of approximately $20,000 per phase event.

The encapsulation (emulsified) chemistry works by forming physical barriers that keep water droplets form coalescing in the fuel. The molecule has a hydrophilic (water-loving or polar) end on one side and a hydrophobic (oil-loving or nonpolar) end on the other side of the molecule. This allows the encapsulating molecule to stay in the fuel, as well as become attracted to the water.

When added to the fuel, the molecule is able to surround the water droplet with its polar sides bonding to the water and having its nonpolar tails extending away from said water droplet and into the fuel. The molecule is able to lower interfacial tension between the fuel and water phases, thereby stabilizing the water droplets and preventing them from coalescing within the fuel.

The increase in water concentration within a fuel tank provides for a hospitable environment for biological growth. What the water is dispersed in encapsulated form, the incidence of biological growth is reduced. Encapsulation will also reduce any corrosive effects of the free water. Encapsulated fuels also have environmental and economic benefits. Water that is encapsulated decreases combustion temperatures and lowers nitrogen oxides (NOx), namely nitrogen dioxide, emissions. Emulsified fuels are effective in simultaneously reducing NOx and particulate emissions, while encapsulated (emulsified) fuel reduces the detritus effects of water leavened fuel.

Free water in said fuel tank or fuel delivery system can form ice crystals in freezing temperatures, thus requiring closure of fuel filters, fuel lines and injectors, and even drastically reducing fuel lubricity, thereby creating a potential for damage to any critical fuel system components. However, the encapsulating chemistry controls the formation of free water. This chemistry works by controlling and eliminating free water from the fuel tank, thereby preventing corrosion in a bottom section of said fuel tanks where water generally collects. Reducing and eliminating the free water from within said fuel tanks prevents the formation of microbial "slime." Additionally, eliminating free water also prevents the formation of a fuel/water interface where microbes can typically grow, and thus create slime that can plug fuel filters and fuel lines.

One of the most important fuel parameters for gasoline is the anti-knock quality, also referred to as the octane rating. Knock occurs when the octane requirement of an engine exceeds the octane quality of the fuel, thus resulting in a metallic clanking noise due to the fluctuations in prevailing pressure. This can ultimately lead to damage of a variety of different critical engine parts, such as, for example, liners, bearings, and pistons.

The anti-knock quality of a fuel is normally rated by its octane number. The chemistry of the octane booster prevents the onset of knock (detonation or pre-ignition). By preventing knock, the effective octane of the fuel is thereby raised. The octane rating of gasoline designates how much the air-fuel mixture can be compressed before it will spontaneously ignite. Gasoline with an optimal octane rating performs best in an engine that is designed to run on that specific octane level.

Fuel producers aim to produce gasoline that has an optimal octane rating, so that said gasoline will meet the specifications for most types of different engines. A plurality of injectors are able to meter a given amount of fuel into a combustion chamber as a piston travels in an upward direction towards a top-dead-center position. As the piston moves in an upward direction, said piston compresses the fuel-air mixture that is already within the cylinder. When the air fuel mixture ignites by the heat of compression rather than because of a spark that is created from a spark plug, this causes knocking in the engine and a loss of power. The knocking sound is caused by two exploding "flame fronts"-one explosion from the pre-ignition of the fuel-air mixture that is caused by compression and the second from the rest of the fuel air mixture being ignited at a slightly different time by the spark plug. The two flame fronts explode and send shock waves through the air of the cylinder, which meet in the combustion chamber and give the knock effect.

The compression ratio of an engine determines the octane rating of the gas that must be used in a particular car. The engine is designed to perform its best with a specific octane rating of gasoline. A "high performance engine" has a higher compression ratio and thus requires a higher-octane fuel in order to prevent it from prematurely igniting fuel before the spark plug ignites the fuel-air mixture. Octane prevents the air-fuel mixture from igniting before the spark plug does it. Gasoline can lose approximately one point to two points in the octane rating due to transport and contamination. The octane boost chemistry brings the rating back to specifications and adjusts the firing of the air-fuel mixture at the proper, desired time, thereby giving the maximum power in which the engine was designed.

In order to ensure that the process of the present invention can be implemented quickly enough to reduce store downtime, a contractor training program has been developed that will supply existing local service technicians with the knowledge that is needed to cure phase events. Each fuel course is developed using an ADDIE Model, which is a systematic approach comprising of five (5) simple phases: (1) Analyze; (2) Design; (3) Develop; (4) Implement; and (5) Evaluate.

BRIEF DESCRIPTION OF THE DRAWINGS/ FIGURES

The foregoing summary, as well as any detailed description of the preferred embodiments, is better understood when read in conjunction with the drawings and figures contained herein. For the purpose of illustrating the invention, the drawings and figures show certain preferred embodiments. It is understood, however, that the invention is not limited to the specific methods and devices disclosed in such drawings or figures.

DETAILED DESCRIPTION OF A PREFERRED EMBODIMENT

Figure 1A:
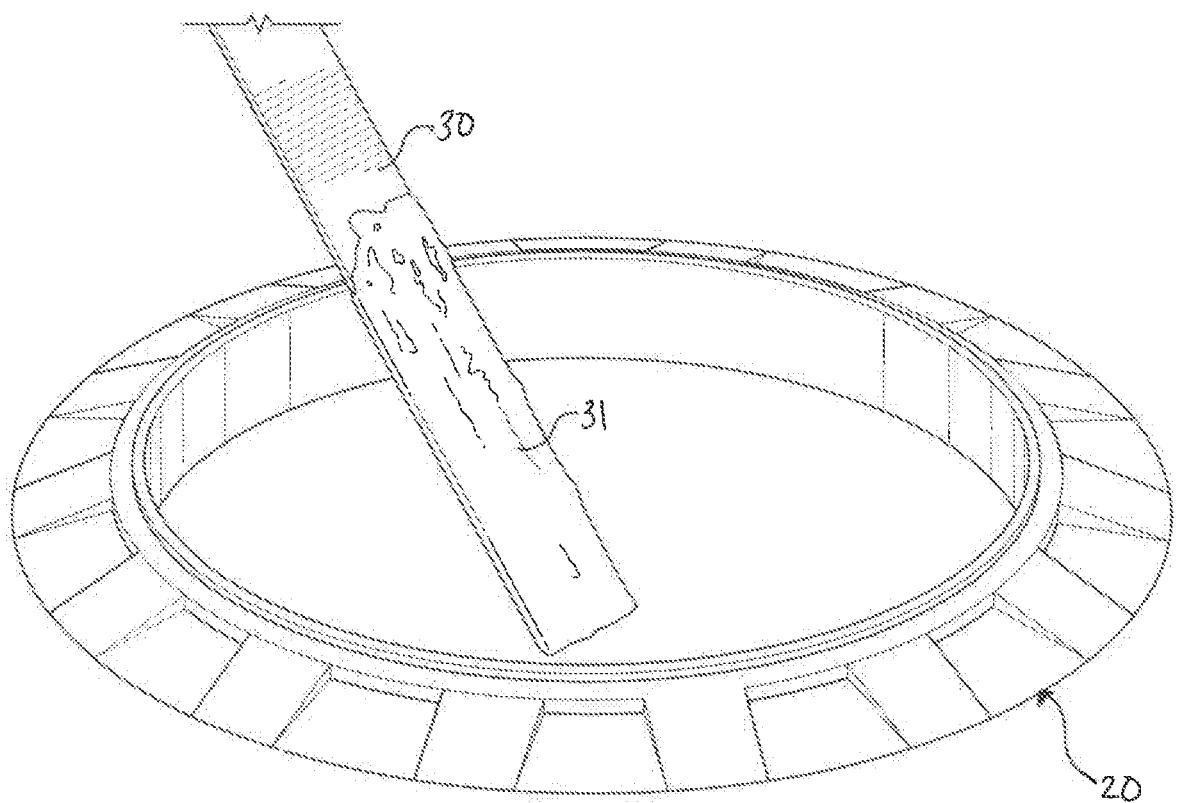
FIG. 1A depicts a side perspective view of a preferred embodiment of a water-detecting paste on a stick that has not changed color prior to being placed into a fuel tank.

Referring to the drawings, the method of the present invention comprises both testing a fuel tank 20 for phase separation and then treating said fuel tank 20 and fuel for phase separation. The method and protocol for testing a fuel tank 20 for phase separation comprises a plurality of events.

An operator 5 will typically arrive on a designated site location and contact store personnel in order to determine the particular issues that said location is having. The operator 5 will pull an electronic monitoring report 50 (such as, for example, a Veeder-Root report) in order to determine if at least one sensor(s) is picking up any indication of free-standing water within a fuel tank 20. Said electronic monitoring report 50 comprises a print-our showing fuel inventory and indicating whether said fuel tank 20 has any free-standing water within said tank 20.

The operator 5 will be able to open said fuel tank 20, wherein said fuel tank 20 comprises a first opening 21 and a second opening 22. Said first opening 21 of said fuel tank 20 comprises a fill tube 23, or a fill pipe, wherein a delivery truck 7 is able to connect to and transfer fuel from said truck 7 into said fuel tank 20. Said second opening 22 of said fuel tank 20 comprises a tank top opening 24 (Automatic Tan Gauge, or "ATG" opening), wherein an electronic probe can be dropped into said fuel tank 20 in order to measure an amount of fuel that is within said tank 20 and to almost be able to measure an amount of water that is located at a bottom 19 of said fuel tank 20.

FIG. 1A depicts a side perspective view of a preferred embodiment of a water-detecting paste 31 placed on a stick 30 prior to being placed into a fuel tank 20. As illustrated in FIG. 1A, prior to said stick 30 being placed within said fuel tank 20, said water-detecting paste 31 has not changed color. In the preferred embodiment, the operator 5 will stick said fuel tank 20 at both said first opening 21 and said second opening 22 with a water-detecting paste 31. Said operator 5 will apply said water-detecting paste 31 in order to determine if any free-standing water is present within said fuel tank 20. By way of illustration, but not limitation, said water-detecting paste 31 can be used from a variety of different manufacturers, such as, for example, Sargel®, Gasoila®, or Kolor-Kut®. Although the method of the present invention is described herein primarily in connection with said particular water-detecting paste 31, it is to be observed that the present invention can be beneficially used with a variety of other different chemicals, as well.

Figure 1B:
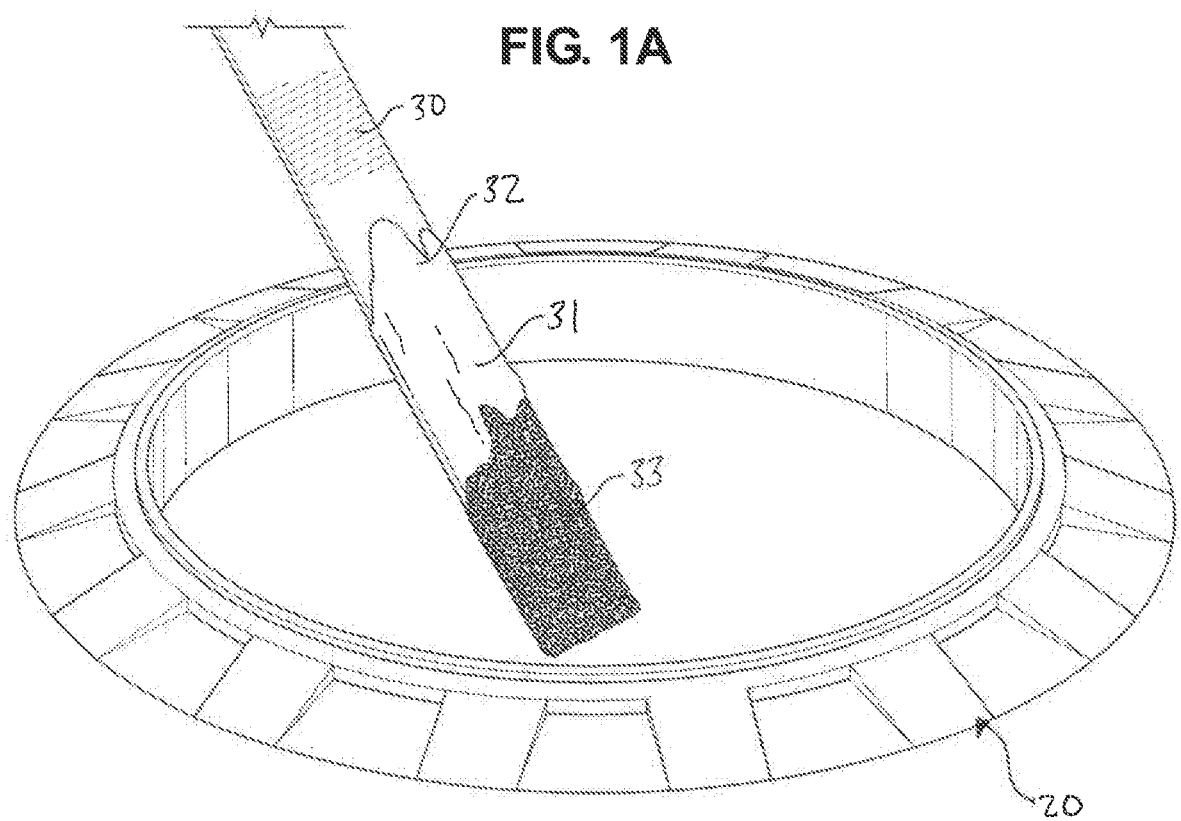
FIG. 1B depicts a side perspective view of a preferred embodiment of a water-detecting paste on a stick that has changed color after being placed into a fuel tank.

FIG. 1B depicts a side perspective view of a preferred embodiment of a water-detecting paste 31 on a stick 30 that has changed color after being placed into a fuel tank 20. After said operator 5 sticks said fuel tank 20 with said water-detecting paste 31, said operator 5 will then take a photograph of the results that appear at both said first opening 21 and said second opening 22 of said fuel tank 20. For example, referring back to FIG. 1A, when said water-detecting paste 31 is first applied, Sargel® is white in color 32. However, as illustrated in FIG. 1B, if water is detected, then Sargel® turns purple in color 33, thereby indicating that water is present in suspension. It is to be noted that other types and brands of water-detecting paste 31 will generally start with a brown color, and then, if water is detected, said pastes will turn a neon yellow color.

Figure 2:
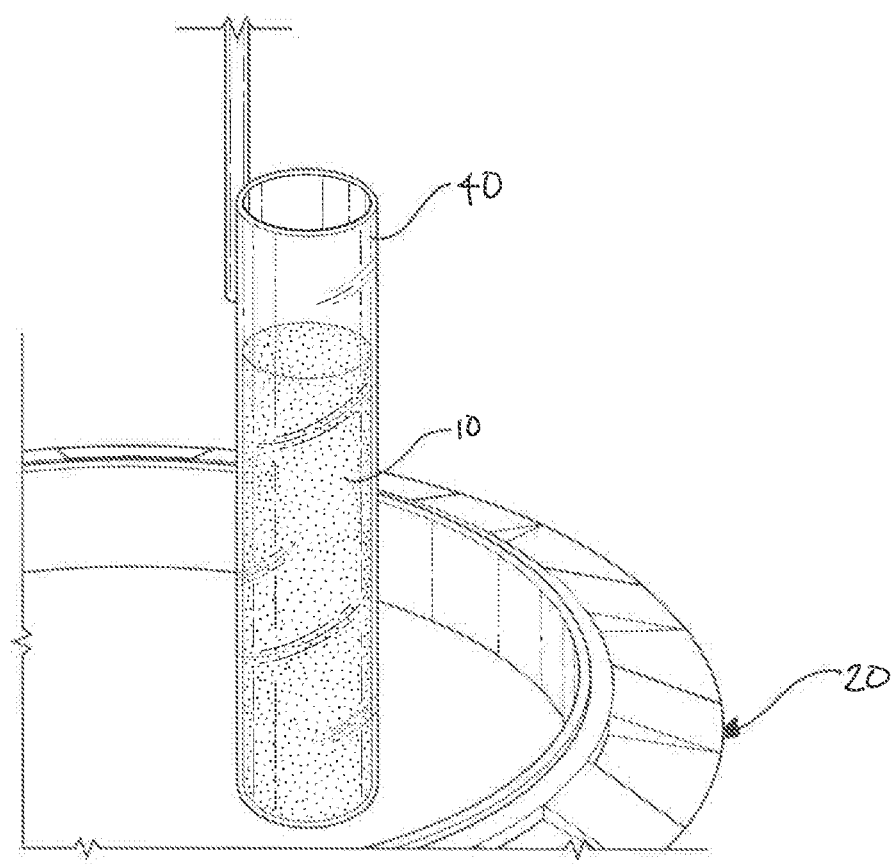
FIG. 2 depicts a side perspective view of a preferred embodiment of a bailer/bacon bomb being placed into a fuel tank in order to pull a variety of fuel samples from said tank.

FIG. 2 depicts a side perspective view of a preferred embodiment of a Bailer/Bacon Bomb 40 being placed into a fuel tank 20 in order to pull a variety of fuel samples 10 from said tank 20. In the preferred embodiment, the operator 5 will use said "Bailer/Bacon Bomb" 40, or any other particular device that is typically used to pull a fuel sample 10 from the bottom location 19 of said fuel tank 20, in order to pull a plurality of fuel samples 10 out of both said first opening 21 and said second opening 22 at three (3) different levels (such as, a bottom level 19, a middle level 18, and a top level 17).

Figure 3:
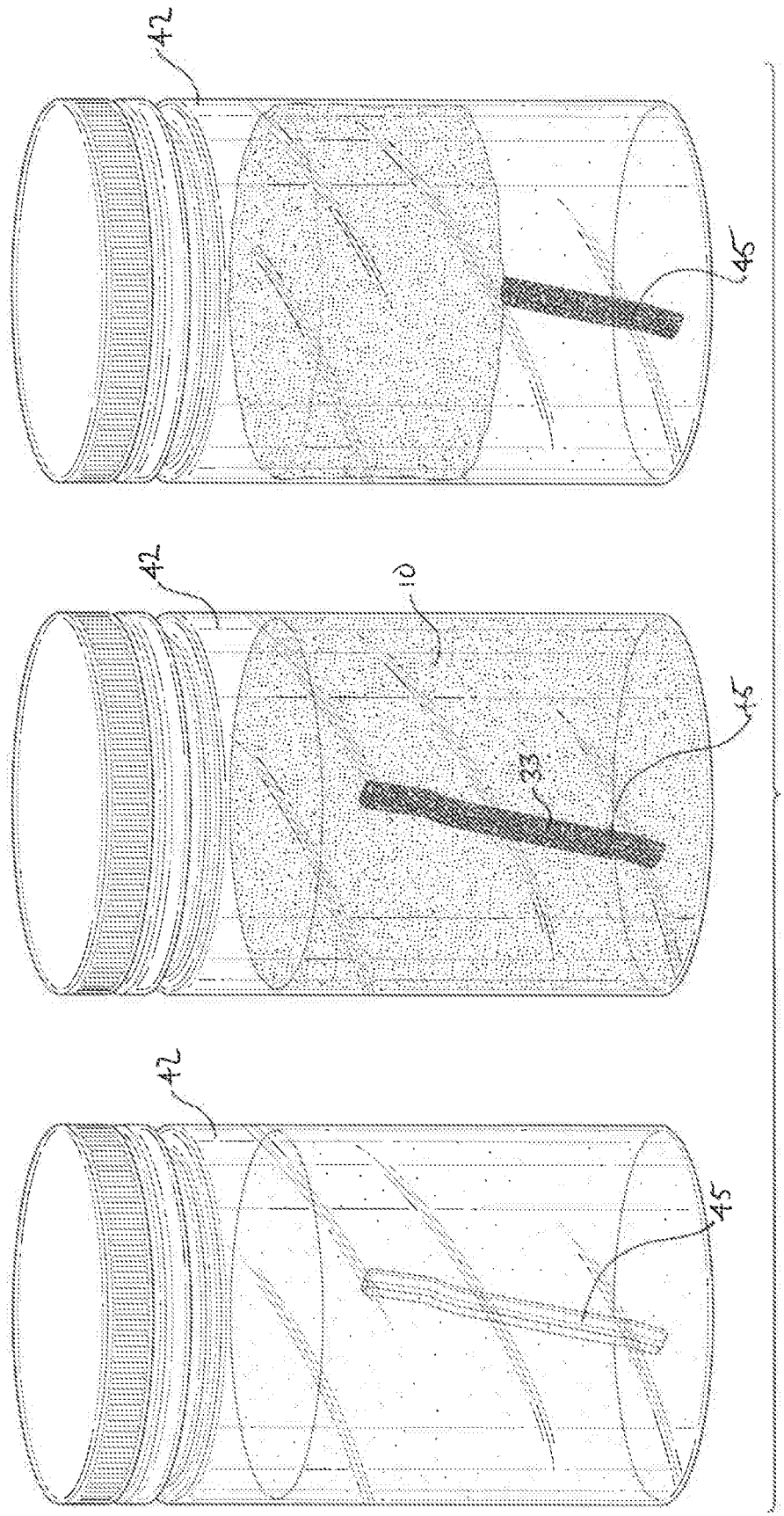
FIG. 3 depicts a side view of a preferred embodiment of a plurality of clear glass jars with each having a fuel sample within said jar in order to visualize any free-standing water and emulsified fuel.

FIG. 3 depicts a side view of a preferred embodiment of a plurality of clear glass jars 42 with each jar 42 having a fuel sample 10 located within said jar 42 in order to visualize any free-standing water and emulsified fuel. In the preferred embodiment, said operator 5 will then put each fuel sample 10 that was pulled from said fuel tank 20 into a separate clear glass jar 42. As such, there will be three (3) separate clear glass jars 42 comprising a fuel sample from each of said three (3) different levels 17, 18, 19 within said fuel tank 20. Said operator 5 will then be able to see any free-standing water and emulsified fuel within said clear glass jars 42.

Figure 4:
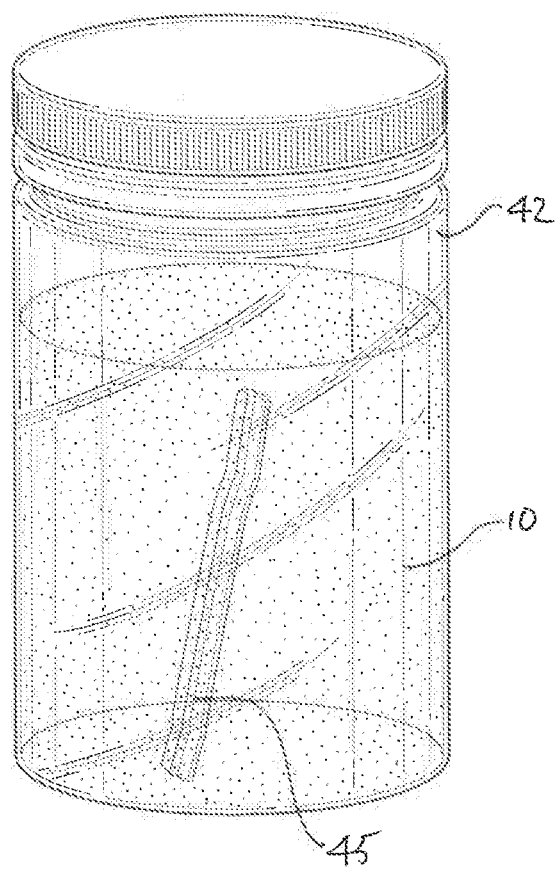
FIG. 4 depicts a side view of a preferred embodiment of a clear glass jar comprising a fuel sample and a zip tie.

FIG. 4 depicts a side view of a preferred embodiment of a clear glass jar 42 comprising a fuel sample 10 and a zip tie 45. In the preferred embodiment, as illustrated in FIG. 4, the operator will take a zip-tie 45, or any other similar piece of plastic exhibiting like characteristics, and put a small amount of water-detecting paste 31 on said plastic 45. Said operator 5 will then place the water-detecting paste 31 dipped plastic 45 into all three (3) glass jars 42. The fuel samples 10 will then remain in ambient atmosphere for approximately twenty (20) to thirty (30) minutes. After thirty (30) minutes has expired, the operator 5 will then check for said water-detecting paste 31 within said fuel sample 10 to turn colors. As such, said operator 5 will then take a photograph of the results after said fuel samples 10 have been sitting in ambient atmosphere for approximately twenty (20) to thirty (30) minutes.

In the preferred embodiment, if the water-detecting paste 31 that is within the fuel samples 10 has turned colors, thereby indicating that water is present in suspension, then the operator 5 will move directly into the treatment process. However, if the water-detecting paste 31 has not turned colors, then said operator 5 will put said fuel samples 10 comprising said water-detecting paste 31 into a bucket of ice for approximately twenty (20) to thirty (30) minutes. After twenty (20) to thirty (30) minutes has expired, said operator 5 will pull said fuel samples 10 out of the ice buckets and then re-check all three (3) fuel samples 10 to see if the water-detecting paste 31 has turned colors. If the water-detecting paste 31 has not turned colors, then the fuel is not phase separated. If the water-detecting paste 31 has turned colors, then the fuel has water in suspension and this will illustrate that fuel that needs to be treated or filtered in order to remove said water out of suspension.

In a preferred embodiment, the method or protocol for a fuel/fuel tank treatment process comprises a plurality of events. To begin the testing process, the operator 5 will re-stick said fuel tank 20 using said water-detecting paste 31 at both said first opening 21 and said second opening 22 of said fuel tank 20 in order to see how much "free standing water" is located in said fuel tank 20. The operator 5 will then re-pull another fuel sample 10 from said bottom level 19 of said fuel tank 20 in order to visually see the "free standing water." Next, the operator 5 will take a "stinger", or any other similar pipe or device (such as, for example, a plastic pipe, or electrical piping/conduit), that is generally used to attach to a fuel pump in order to remove and/or vacuum the water out of said fuel tank.

Said operator will then remove any water from both said first opening 21 and said second opening 22 of said fuel tank 20 (Fill and ATG). Next, the operator 5 will re-stick said fuel tank 20 using water-detecting paste 31 at both said first opening 21 and said second opening 22 in order to see if all of the free standing water has been removed. The operator 5 will repeat this process until all of the water-detecting paste 31 indicates that there is "no water" at both first opening 21 and second opening 22.

After this process has been completed, said operator 5 will let said fuel tank 20 settle for approximately ten (10) to twenty (20) minutes and then re-stick said fuel tank 20 in order to confirm that all of the free standing water has been removed from both first opening 21 and second opening 22. Said operator 5 will then add a "smart stinger" that will go the complete length of said fuel tank 20 and remove all of the water in-between said first (fill) 21 and said second 22 (ATG) openings. A smart stinger generally comprises approximately two (2) to ten (10) ft. pieces of pipe connected together, wherein at least one piece of pipe is heated and bent in order for it to bend when it is placed down into a four (4) inch riser opening. This bend makes sure that an end of the pipe remains on a bottom 19 of the fuel tank 20 in order to remove all of the water and any debris that is sitting on the bottom 19 of the fuel tank 20. The operator 5 will then repeat this process until there is no water left coming out of said fuel tank 20.

During the water removal and/or vacuum process, the operator 5 can take a fuel sample 10 out of the return hose to check and see if any emulsified fuel is now being removed from said fuel tank 20. If emulsified fuel is being removed from said fuel tank 20, the operator 5 will continue this process of removing/vacuuming emulsified fuel out of said fuel tank 20 and verify the results by pulling several fuel samples 10 from said return hose. If all of the water and emulsified fuel has been removed from the fuel tank 20, the operator 5 will let the fuel tank 20 settle again for approximately ten (10) to twenty (20) minutes and then pull another bottom level sample from said fuel tank 20. If there is no water or emulsified fuel remaining in the fuel tank 20, the operator 5 will then begin the chemical treatment process.

In the preferred embodiment, the first step of the chemical treatment process is to determine the mixing ratio of chemical to fuel, otherwise referred to as the "treatment ratio."

The amount of time that it takes for the water-detecting paste 31 to change colors (or the reaction time) is based on the amount of free-standing water that is in suspension. As such, the amount of water that is in suspension determines the amount of chemical that needs to be added to the fuel, thereby providing the specific treatment ratio for the particular amount of water that is determined to be located within suspension.

As a result, the percentage of water is determined by the amount of time (how quickly) the color of the water-detecting paste 31 changes color. However, it is to be understood that any dependent variables (such as, for example, type of fuel, concentration of ethanol, or temperature) could influence the rate, and thus, treatment ratio. As such, the linear equation for the treatment ratio is $y = -0.048x + 0.8937$, where $y = \%$ water, and $x =$ time in minutes.

Figure 5:
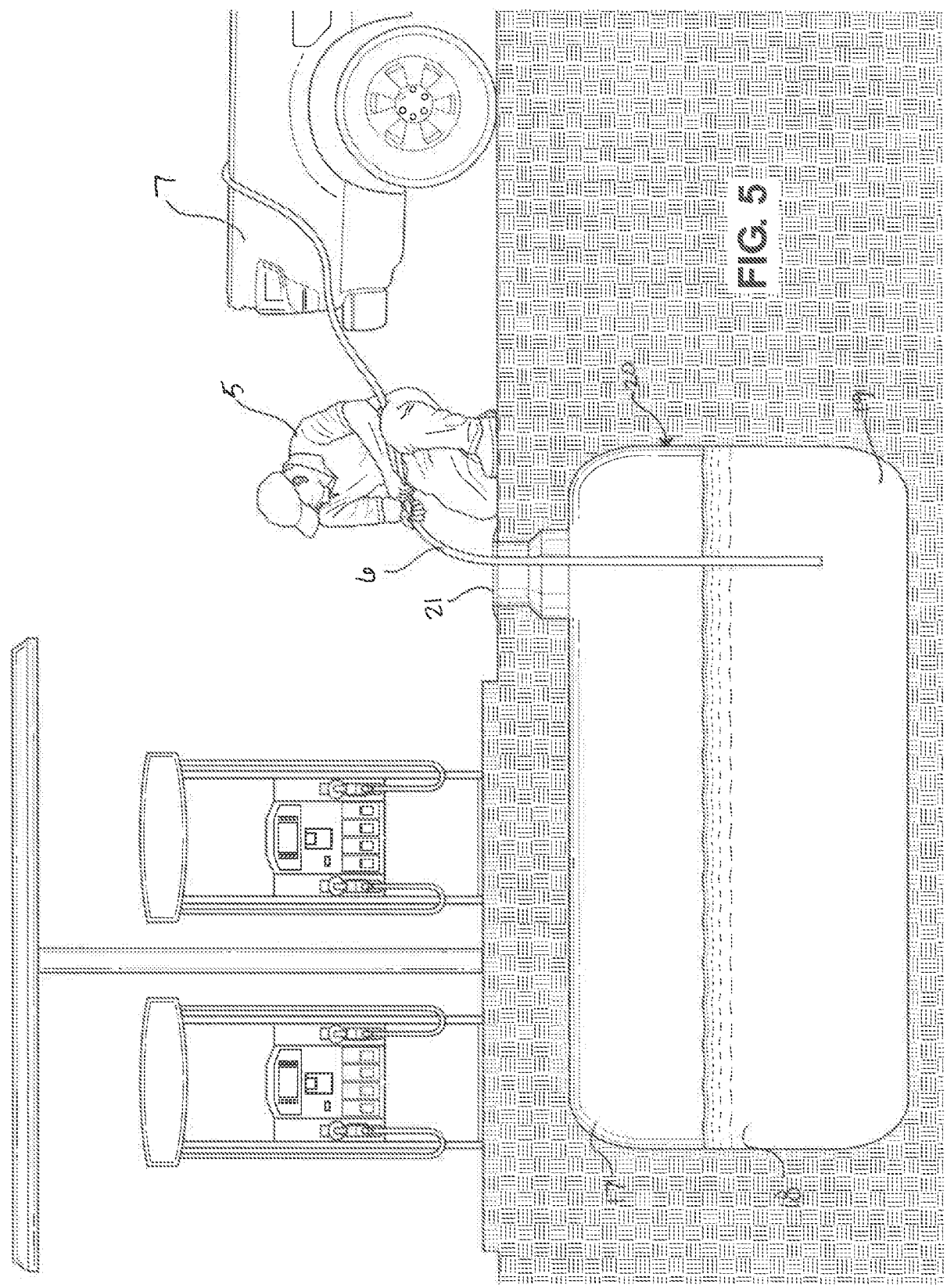
FIG. 5 depicts a side view of a preferred embodiment of a chemical treatment being added into a fuel tank and then agitated.

FIG. 5 depicts a side view of a preferred embodiment of a chemical treatment being added into a fuel tank 20 and then agitated in order to ensure that said chemical is evenly dispersed within said tank 20. As depicted in FIG. 5, in the preferred embodiment, once the proper treatment ratio has been determined, the fuel tank 20 is then ready for chemical treatment. The chemical treatment process is then started by splashing a desired amount of chemical on "top" of the fuel. Since the chemical is heavier than the fuel, the chemical will work its way down through the particular fuel levels within said fuel tank. The operator 5 will then splash the chemical on both said first opening 21 and said second opening 22 of said fuel tank 20 and have the return hose 6 in the liquid fuel agitate the fuel tank 20.

Referring back to FIG. 4, after the fuel tank 20 settles for approximately five (5) to ten (10) minutes, the operator 5 will repeat this process, but with the chemical treatment process in the middle 18 of the fuel tank 20. Then, after the tank 20 settles for approximately another five (5) to (10) minutes, then operator 5 will again repeat this process, but with the chemical treatment process at the bottom 19 of the fuel tank 20. If necessary, the operator can repeat this chemical treatment process. The operator 5 will let the tank 20 settle for another five (5) to (10) minutes, pull the new fuel samples 10 from the bottom 19, middle 18, and top 17 levels of said fuel tank 20, and then test said fuel at all levels for phase separation and then repeat the protocol steps.

Figure 6:
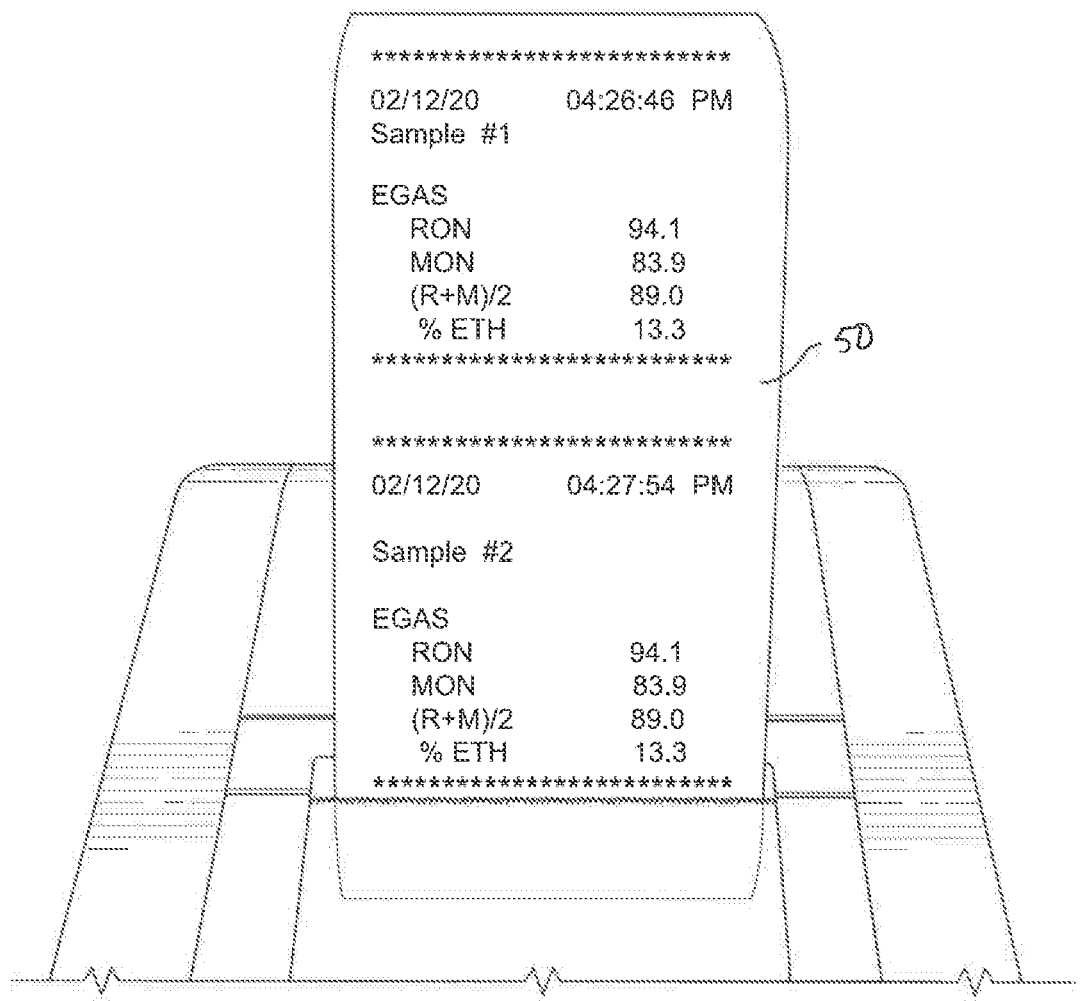
FIG. 6 depicts a front view of a preferred embodiment of an octane rating being checked.

FIG. 6 depicts a front view of a preferred embodiment of an octane rating being checked. In the preferred embodiment, if water-detecting paste 31 shows that there has been no color change, and thus, no water present in suspension, new electronic reports 50 (Veeder-Root) should be obtained. The operator 5 can then move on to test the octane levels within said fuel. The new electronic report 50 that is taken after the chemical treatment process has occurred shows the fuel inventory and indicates whether said fuel tank 20 has any free-standing water remaining. As such, and as illustrated in FIG. 6, the operator 5 can use a ZELTEX octane analyzer, or any other similar device exhibiting similar characteristics and performing similar functions, in order to obtain a new electronic report 50 and confirm specific octane levels of said fuel. A ZELTEX octane analyzer is a device that uses a variety of algorithms to determine octane levels in fuel. Said device is typically used by at least forty-five (45) states or more in order to determine octane levels of a particular fuel site.

The above-described invention has a number of particular features that should preferably be employed in combination, although each is useful separately without departure from the scope of the invention. While the preferred embodiment of the present invention is shown and described herein, it will be understood that the invention may be embodied otherwise than herein specifically illustrated or described, and that certain changes in form and arrangement of parts and the specific manner of practicing the invention may be made within the underlying idea or principles of the invention.

What is claimed:

1. A method of testing a fuel tank and fuel within said fuel tank for phase separation and free-standing water and then treating said fuel tank and said fuel for phase separation, comprising:
   a) inserting a water-detecting paste by way of a collapsible measuring stick into said fuel tank at a first opening and a second opening in order to determine if any free-standing water is present anywhere within said fuel tank or within said fuel;
   b) observing any color change of said water-detecting paste;
   c) pulling a plurality of fuel samples from said fuel tank;
   d) placing said fuel samples in a plurality of separate clear containers;
   e) placing a piece of plastic within each clear container, wherein each piece of said plastic comprises an amount of water-detecting paste;
   f) observing both any color change of said water-detecting paste on each piece of plastic within each container and an amount of time it takes for said water-detecting paste to change color;
   g) adding a chemical treatment to said fuel within said fuel tank in order to reduce or eliminate the presence of any water in suspension within said fuel and said fuel tank;
   h) agitating said fuel tank to evenly disperse said chemical treatment;
   i) allowing said fuel tank to settle;
   j) pulling a plurality of additional fuel samples from said fuel tank in order to re-test for phase separation with said water-detecting paste in order to determine if additional chemical treatment of said fuel is needed; and
   k) checking an octane rating of said fuel after said water-detecting paste indicates that no more free-standing water or water in suspension is present within said fuel and said fuel tank.

2. The method of claim 1, wherein an amount of said chemical treatment that is used to reduce or eliminate the presence of any water within said fuel and said fuel tank is determined based on an amount of water that is present in suspension within said fuel tank.

3. The method of claim 2, wherein said amount of water that is present in suspension within said fuel tank is determined based on an amount of time that it takes for said water-detecting paste to change color after said water-detecting paste is inserted into each of said fuel samples located within each of said separate clear containers.

4. The method of claim 1, further comprising pulling said fuel samples from said fuel tank using a Bailer/Bacon Bomb.

5. The method of claim 4, wherein said fuel samples are pulled from a bottom level, a middle level, and a top level of said fuel tank.

6. The method of claim 5, wherein said fuel samples from said bottom level, said middle level, and said top level of said fuel tank are each placed in separate clear containers.

* * * * *